United States Patent [19]

Ellgen

[11] Patent Number: 5,120,524
[45] Date of Patent: Jun. 9, 1992

[54] CO-PRODUCTION OF HYDROGEN PEROXIDE AND A USEFUL ESTER

[75] Inventor: Paul C. Ellgen, Oklahoma City, Okla.

[73] Assignee: Kerr-McGee Corporation, Oklahoma City, Okla.

[21] Appl. No.: 732,384

[22] Filed: Jul. 18, 1991

[51] Int. Cl.⁵ .................. C01B 15/023; C07C 69/34; C07C 69/52; C07C 69/96

[52] U.S. Cl. .................................. 423/588; 558/260; 560/190

[58] Field of Search .................. 423/588; 560/190; 558/260

[56] References Cited

U.S. PATENT DOCUMENTS

| | | | |
|---|---|---|---|
| 4,005,130 | 1/1977 | Zehner | 260/485 R |
| 4,281,174 | 7/1981 | Current | 560/204 |
| 4,336,238 | 6/1982 | Dalton, Jr. | 423/584 |
| 4,379,939 | 4/1983 | Radel et al. | 560/193 |
| 4,393,038 | 7/1983 | Sun et al. | 423/584 |
| 4,428,922 | 1/1984 | Hopkins | 423/588 |
| 4,454,342 | 6/1984 | Gaffney et al. | 560/190 |
| 4,571,435 | 2/1986 | Radel et al. | 564/135 |
| 4,614,832 | 9/1986 | Current | 560/204 |
| 4,681,751 | 7/1987 | Gosser | 423/584 |
| 4,772,458 | 9/1988 | Gosser et al. | 423/584 |
| 4,832,938 | 5/1989 | Gosser et al. | 423/584 |
| 4,889,705 | 12/1989 | Gosser | 423/584 |

Primary Examiner—Wayne Langel
Attorney, Agent, or Firm—Herbert M. Hanegan

[57] ABSTRACT

A process for co-producing hydrogen peroxide and another useful product, namely either an oxalate ester or a carbonate ester product, is provided. The process comprises reacting a saturated monohydric alcohol with carbon monoxide and a quinone to form an oxalate ester or a carbonate ester product and hydroquinone. The hydroquinone is then reacted with oxygen to form hydrogen peroxide and a quinone. The quinone from the second reaction can be recycled to the alcohol-carbon monoxide first reaction.

12 Claims, No Drawings

CO-PRODUCTION OF HYDROGEN PEROXIDE AND A USEFUL ESTER

BACKGROUND OF THE INVENTION

1. Field of the Invention

The present invention relates generally to the coproduction of hydrogen peroxide and another useful product, and more particularly, to an improved two-step process of producing hydrogen peroxide wherein an oxalate ester or a carbonate ester is also produced. 2. Description of the Prior Art The production of hydrogen peroxide has generally been accomplished heretofore using the "anthraquinone process". The anthraquinone process is a two step process wherein in the first step, a substituted or unsubstituted anthraquinone is reduced with molecular hydrogen in the presence of a catalyst to an anthrahydroquinone. The anthrahydroquinone is separated from the catalyst and then reacted with air in the second step to form hydrogen peroxide and the starting anthraquinone which is recycled to the first step.

A number of processes have also been developed which involve the production of an oxalate ester by the oxidative coupling of carbon monoxide with an alcohol in the presence of a quinone. For example, U.S. Pat. No. 4,005,130 issued Jan. 25, 1977 discloses the preparation of an oxalate ester by the oxidative coupling of carbon monoxide and an alcohol in the presence of a catalytic amount of a copper, nickel, cadmium, cobalt or zinc metal salt and at least a stoichiometric amount of an unsubstituted or halogen substituted quinone.

U.S. Pat. No. 4,379,939 to Radel et al. discloses the production of an oxalate ester by the oxidative carbonylation of alcohol with carbon monoxide in the presence of a substituted or unsubstituted quinone, the production of oxamide (a potential fertilizer) from the oxalate ester, and the regeneration of the starting quinone by oxidation of the produced hydroquinone.

By the present invention, an improved two-step process for producing hydrogen peroxide is provided wherein another useful product in addition to the hydrogen peroxide is produced, i.e., either a product substantially comprised of an oxalate ester or a product substantially comprised of a carbonate ester.

SUMMARY OF THE INVENTION

The present invention provides a process for coproducing hydrogen peroxide and an oxalate and/or carbonate ester. The first step of the process comprises catalytically reacting a saturated monohydric alcohol having from 1 to 10 carbon atoms with carbon monoxide and a quinone at selected reaction conditions to form a substantially oxalate ester product or a substantially carbonate ester product and hydroquinone. In a second step, the hydroquinone produced in the first step is reacted with oxygen to form hydrogen peroxide and a quinone. The quinone can be recycled as the starting quinone in the first step.

It is, therefore, a general object of the present invention to provide a process for the co-production of hydrogen peroxide and an oxalate or carbonate ester.

Other and further objects, features and advantages of the present invention will be readily apparent to those skilled in the art upon a reading of the description of preferred embodiments which follows.

DESCRIPTION OF PREFERRED EMBODIMENTS

As mentioned above, a process which has been heretofore known and used for the manufacture of hydrogen peroxide involves the hydrogenation and oxidation of a quinone, usually anthraquinone. In a first step of the process, a substituted or unsubstituted quinone, e.g., anthraquinone is reduced with molecular hydrogen in the presence of a catalyst. This reaction utilizing anthraquinone is illustrated as follows:

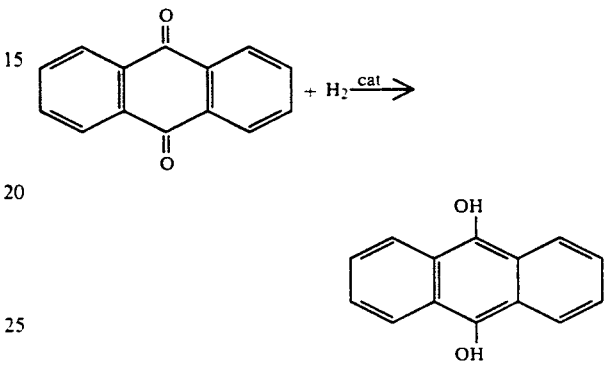

In a second step the resulting hydrogenated quinone is reacted with oxygen or air to form an intermediate which decomposes rapidly to hydrogen peroxide and the starting quinone. This reaction is illustrated when anthrahydroquinone is involved as follows:

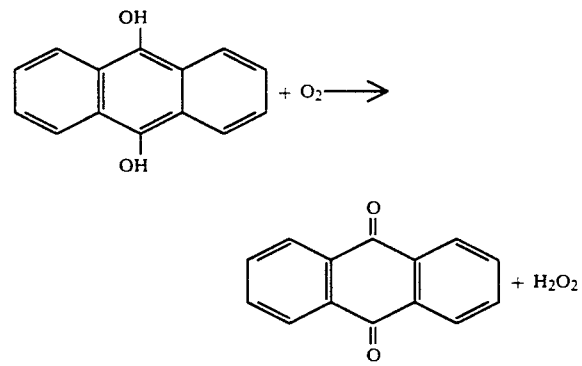

The quinone produced in the second reaction, e.g., anthraquinone, can be recycled as the starting quinone for the first reaction. Except for losses caused by side reactions, there is no net consumption of materials in the process other than hydrogen and oxygen.

As described in U.S. Pat. No. 4,005,130 issued Jan. 25, 1977, which is incorporated herein by reference, oxalate esters can be prepared by the oxidative carbonylation of alcohols with carbon monoxide in the presence of a quinone. That is, an oxalate ester is produced by reacting, under relatively anhydrous liquid phase conditions, an alcohol with carbon monoxide and an unsubstituted or substituted quinone at elevated temperature and pressure and in the presence of a catalytic amount of a catalyst selected from a copper, cobalt, cadmium, nickel or zinc halide, oxalate, trifluoroacetate or acetate salt.

By the present invention, an improved two-step process for producing hydrogen peroxide is provided wherein another useful product is co-produced, namely a substantially oxalate ester product or a substantially carbonate ester product. Oxalate esters are useful chemical intermediates. For example, they can be hydrolyzed to oxalic acid, hydrogenated to ethylene glycol and ammoniated to oxamide. Oxalic acid is useful as a sequestering agent in metal treatment, and as a bleaching agent in textile processing and the paper industry. Ethylene glycol is utilized as antifreeze and as a polymer intermediate in the manufacture of polyester fibers and fabrics, and oxamide is useful as a slow release source of fertilizer nitrogen. Oxalate esters have high fuel blending-octane numbers and can also be utilized as fuel-additives. Carbonate esters can also be used as octane enhancing components in gasoline. In addition, carbonate esters are valuable chemical intermediates in that they are strong alkylating agents.

The process of the present invention utilizes a first step comprised of catalytically reacting a saturated monohydric alcohol having from 1 to 10 carbon atoms with carbon monoxide and a substituted or unsubstituted quinone at selected reaction conditions to selectively form an oxalate ester or a carbonate ester and hydroquinone. The reaction is illustrated using unsubstituted quinone as follows:

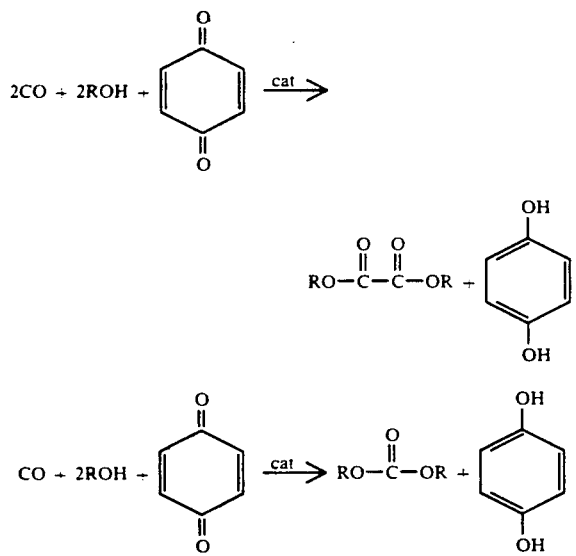

While a variety of alcohols (ROH) can be utilized in carrying out the reaction, they are preferably selected from monohydric alcohols having from 1 to 10 carbon atoms. Preferred such alcohols are methyl alcohol, ethyl alcohol, isopropyl alcohol, normalbutyl alcohol and mixtures thereof. Of these, methyl alcohol is the most preferred.

In addition to unsubstituted quinone (2,5-cyclohexadiene-1,4-dione), a variety of substituted quinone compounds can be utilized. Preferably, the quinone compound is selected from the group consisting of quinone, alkyl-, aryl- and halogen substituted derivatives thereof and mixtures of such compounds. The most preferred quinone compound is anthraquinone.

A variety of metal catalysts can be employed in the first step of the process including supported metals, metal salts and other metal compounds or complexes wherein the metal is copper, nickel, cadmium, cobalt, zinc, palladium, rhodium and platinum. The salts can be halides, oxalates, acetates and others, and mixtures of the metal catalysts can be used.

The oxidative coupling reaction of the alcohol and carbon monoxide can be carried out, either continuously or in batch in a conventional high pressure and temperature reactor, and by controlling the reaction conditions, either a substantially oxalate ester product or a substantially carbonate ester product can be selectively produced. For example, when it is desired to produce an oxalate ester, e.g., dimethyl oxalate, the reaction is carried out under the liquid phase conditions of the alcohol, quinone and catalyst at a carbon monoxide pressure in the range of from about 200 psig to about 5000 psig, preferably from about 1500 psig to 2000 psig and at a temperature in the range of from about 80° C. to about 200° C., preferably from about 100° C. to about 150° C. While it is not necessary for the medium to be strictly anhydrous, the water content should be kept to a minimum in order to achieve high selectivity to the oxalate ester. Desirably the water content is less than 2%, more desirably less than 1%, and preferably less than 0.5%. The catalyst utilized is preferably palladium chloride employed in an amount between about 0.01 to about 2 percent by weight of the alcohol.

When the production of a substantially carbonate ester product, e.g., dimethylcarbonate, is desired, a palladium chloride catalyst is utilized in an amount between about 0.1 to about 2 percent by weight of the alcohol, and the reaction is carried out at a pressure in the range of from about 0.1 psig to about 200 psig, preferably from about 1 psig to about 150 psig, and at a temperature in the range of from about 80° C. to about 200° C., preferably from about 100° C. to about 150° C. The water content is carefully controlled between about 2% and about 20% by weight and preferably between about 2% and about 6%. When either the oxalate ester or the carbonate ester is produced, a high yield and good selectivity are obtained.

The second step of the process of the present invention comprises reacting the hydrogenated quinone produced in the first step with oxygen to form hydrogen peroxide and a quinone. As mentioned above, an intermediate is formed which decomposes rapidly to hydrogen peroxide and the quinone. The reaction when the hydroquinone is unsubstituted hydroquinone is as follows:

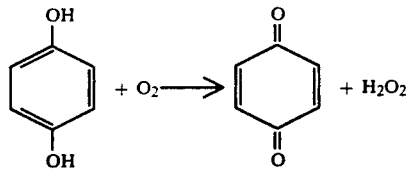

The reaction is carried out in a second conventional reactor at a pressure in the range of from about 0.1 psig to about 150 psig and at a temperature in the range of from about 80° C. to about 130° C.

The quinone produced in the second step can be recycled as a starting quinone material in the reaction of the first step. As will be understood by those skilled in the art, the oxygen utilized in the second step reaction can be pure oxygen or air, with air being the most preferred from an economical standpoint.

Thus, the process of the present invention comprises the steps of first catalytically reacting a saturated monohydric alcohol having from 1 to 10 carbon atoms with carbon monoxide and a quinone at selected reaction conditions to form an oxalate ester or a carbonate ester and hydroquinone followed by the second step of reacting the hydroquinone produced in the first step with oxygen to form hydrogen peroxide and a quinone. The quinone produced in the reaction of the second step can be recycled as the starting quinone for the reaction of the first step. As stated above, the preferred monohydric alcohol is methyl alcohol and the preferred quinone is anthraquinone. The products produced in addition to hydrogen peroxide utilizing such preferred starting materials are either substantially dimethyl oxalate or substantially dimethyl carbonate products.

In order to further illustrate the improved process of the present invention, the following example is given.

EXAMPLE I

A stainless steel autoclave is charged with 20.8 grams of anthraquinone, 0.5 grams of palladium chloride, and 100 grams of normal butanol. The reactor is purged with nitrogen. The reactor is pressured to 1500 psig with carbon monoxide. The temperature of the reactor and contents is increased to 120° C. These conditions are maintained until carbon monoxide uptake ceases. The reactor is cooled to ambient temperature, carbon monoxide is vented, and the solution is analyzed. The yields of dibutyl oxalate and dibutyl carbonate are 70% and 6%, respectively, based on anthraquinone charged. The yield of anthrahydroquinone is 75% based on anthraquinone charged.

EXAMPLE II

The solution obtained in Example I is passed through a mixed bed of cationic and anionic exchange resins to remove palladium-containing species. The palladium-free solution is transferred to a round-bottom flask and warmed to 50° C. A stream of air is bubbled through the solution for one hour. The flask is cooled to the ambient temperature and analyzed for hydrogen peroxide. The yield of hydrogen peroxide is 80% based on anthrahydroquinone charged to the round-bottom flask.

Thus, the present invention is well adapted to carry out the objects and attain the ends and advantages mentioned as well as those which are inherent therein. While numerous changes in reaction conditions, reactants, catalysts and other aspects of the process may be made by those skilled in the art, such changes are encompassed within the spirit of this invention as defined by the appended claims.

What is claimed is:

1. A process for co-producing hydrogen peroxide and a predominantly oxalate ester product comprising:
   (a) reacting a saturated monohydric alcohol having from 1 to 10 carbon atoms with carbon monoxide and a quinone in the presence of a palladium chloride catalyst at a pressure in the range of from about 200 psig to about 5000 psig and a temperature in the range of from about 80° C. to about 200° C. to form said predominantly oxalate ester product and hydroquinone;
   (b) reacting the hydroquinone produced in step (a) with oxygen to form hydrogen peroxide and a quinone at a pressure in the range of from about 0.1 psig to about 150 psig and at a temperature in the range of from about 80° C. to about 130° C.; and
   (c) recycling the quinone produced in step (b) to the reaction of step (a).

2. The process of claim 1 wherein said alcohol is selected from the group consisting of methyl alcohol, ethyl alcohol, isopropyl alcohol, n-butyl alcohol and mixtures thereof.

3. The process of claim 2 wherein said alcohol is methyl alcohol.

4. The process of claim 2 wherein said quinone is selected from the group consisting of 2,5-cyclohexadiene-1,4-dione, alkyl-, aryl- and halogen substituted derivatives thereof and mixtures of such compounds.

5. The process of claim 3 wherein said quinone is anthraquinone.

6. A process for co-producing hydrogen peroxide and a predominantly carbonate ester product comprising:
   (a) reacting a saturated monohydric alcohol having from 1 to 10 carbon atoms with carbon monoxide and a quinone in the presence of a palladium chloride catalyst at a pressure in the range of from about 0.1 psig top about 200 psig and a temperature in the range of from about 80° C. to about 200° C. to form a predominantly carbonate ester product and hydroquinone;
   (b) reacting the hydroquinone produced in step (a) with oxygen to form hydrogen peroxide and a quinone at a pressure in the range of from about 0.1 psig to about 150 psig and at a temperature in the range of from about 80° C. to about 130° C.; and
   (c) recycling the quinone produced in step (b) to the reaction of step (a).

7. The process of claim 6 wherein said alcohol is selected from the group consisting of methyl alcohol, ethyl alcohol, isopropyl alcohol, n-butyl alcohol and mixtures thereof.

8. The process of claim 7 wherein said alcohol is methyl alcohol.

9. The process of claim 7 wherein said quinone is selected from the group consisting of 2,5-cyclohexadiene-1,4-dione, alkyl-, aryl- and halogen substituted derivatives thereof and mixtures of such compounds.

10. The process of claim 8 wherein said quinone is anthraquinone.

11. A process for producing hydrogen peroxide and a predominantly carbonate ester product comprising the steps of:
    (a) catalytically reacting a saturated monohydric alcohol having from 1 to 10 carbon atoms with carbon monoxide and a substituted or unsubstituted quinone at selected reaction conditions to form a predominantly carbonate ester product and hydroquinone; and
    (b) reacting the hydroquinone produced in step (a) with oxygen to form hydrogen peroxide and a quinone.

12. The process of claim 11 wherein said process is further characterized to include the step of recycling the quinone produced in step (b) to the reaction of step (a).

* * * * *